(12) United States Patent
Rodriguez

(10) Patent No.: US 8,903,522 B1
(45) Date of Patent: Dec. 2, 2014

(54) ONLINE PLATFORM FOR MAINTAINING MULTIDISCIPLINARY SPORT PERFORMANCE STATISTICS AND COMPUTING PERFORMANCE FORECASTS

(71) Applicant: Beat Your Mark Group Limited, Malta (EM)

(72) Inventor: Federico Rodriguez, Palma de Mallorca (ES)

(73) Assignee: Beat Your Mark Group Limited, Birkirkara (MT)

( * ) Notice: Subject to any disclaimer, the term of this patent is extended or adjusted under 35 U.S.C. 154(b) by 0 days.

(21) Appl. No.: 14/466,350

(22) Filed: Aug. 22, 2014

Related U.S. Application Data

(60) Provisional application No. 62/012,877, filed on Jun. 16, 2014.

(51) Int. Cl.
- *G06F 19/00* (2011.01)
- *G06K 9/00* (2006.01)
- *A63B 71/06* (2006.01)

(52) U.S. Cl.
CPC ........ *G06K 9/00342* (2013.01); *A63B 71/0616* (2013.01)
USPC ................................. 700/91; 463/7

(58) Field of Classification Search
CPC ........... A63B 24/0021; A63B 24/0062; A63B 71/06; A63B 71/0605; A63B 71/0161; A63F 13/12; A63D 5/04
USPC ................... 700/91–93; 463/1, 7, 8; 473/409; 434/247, 254, 255; 482/8, 9
See application file for complete search history.

(56) References Cited

U.S. PATENT DOCUMENTS

| | | | | |
|---|---|---|---|---|
| 6,885,971 B2 * | 4/2005 | Vock et al. | | 702/182 |
| 7,901,292 B1 * | 3/2011 | Uhlir et al. | | 463/42 |
| 8,182,348 B2 * | 5/2012 | Uhlir et al. | | 463/59 |
| 2002/0161461 A1 * | 10/2002 | Lobb et al. | | 700/91 |
| 2004/0225467 A1 * | 11/2004 | Vock et al. | | 702/142 |
| 2005/0014113 A1 * | 1/2005 | Fleck et al. | | 434/247 |
| 2008/0096726 A1 * | 4/2008 | Riley et al. | | 482/8 |
| 2008/0188330 A1 * | 8/2008 | Doherty et al. | | 473/407 |
| 2008/0200284 A1 * | 8/2008 | Doherty et al. | | 473/407 |
| 2009/0149974 A1 * | 6/2009 | Storch et al. | | 700/91 |
| 2009/0297627 A1 * | 12/2009 | Tanelian | | 424/643 |
| 2010/0004097 A1 * | 1/2010 | D'Eredita | | 482/8 |
| 2010/0087936 A1 * | 4/2010 | Roullier | | 700/91 |
| 2011/0145740 A1 * | 6/2011 | McCue | | 715/764 |
| 2011/0230986 A1 * | 9/2011 | Lafortune et al. | | 700/93 |
| 2011/0250937 A1 * | 10/2011 | Hubbard et al. | | 463/6 |
| 2012/0310389 A1 * | 12/2012 | Martin | | 700/91 |
| 2012/0324010 A1 * | 12/2012 | Pinches | | 709/204 |
| 2013/0040272 A1 * | 2/2013 | Booher | | 434/254 |
| 2013/0053990 A1 * | 2/2013 | Ackland | | 700/91 |
| 2013/0238106 A1 * | 9/2013 | Ellis et al. | | 700/91 |
| 2013/0282640 A1 * | 10/2013 | LaPadula et al. | | 706/46 |

* cited by examiner

*Primary Examiner* — Milap Shah
(74) *Attorney, Agent, or Firm* — Choate, Hall & Stewart LLP; William R. Haulbrook; T. Paul Tanpitukpongse

(57) ABSTRACT

The present disclosure describes a platform that allows individual users to maintain personal performance statistics, which, collectively, are used to determine and update difficulty ratings for various multi-stage sport courses. Ratings are determined for each leg of a given course. The platform enables a user to predict his or her performance on an unfamiliar course based on course ratings and the user's historical performance on other courses.

20 Claims, 4 Drawing Sheets

ONLINE PLATFORM FOR MAINTAINING MULTIDISCIPLINARY SPORT PERFORMANCE STATISTICS AND COMPUTING PERFORMANCE FORECASTS

RELATED APPLICATIONS

The present application claims priority to and the benefit of U.S. Provisional Application Ser. No. 62/012,877, filed Jun. 16, 2014.

BACKGROUND

Individuals who participate in multiple stage sporting activities, such as triathlons, biathlons, and the like, may not reside in the particular location of a competition in which they wish to compete. Traditionally, individuals must train for a competition on local courses or physically move to the location of the upcoming competition in order to train for it. Usually, an individual has difficulty estimating, to a high degree of accuracy, how well they will be able to perform on an unfamiliar course.

SUMMARY

The present disclosure addresses this difficulty by providing a platform for individuals to maintain personal performance statistics, which, collectively, are used to determine and update difficulty ratings for various multi-stage sport courses. The platform enables a user to predict his or her performance on an unfamiliar course based on course ratings and the individual's historical performance on other courses.

Furthermore, the platform determines and updates ratings for each leg of a given course, and allows a user to predict his or her performance on each leg of the course. Because an individual's performance level often varies for each of the multiple legs of a given competition (e.g., the swimming, cycling, and running legs of a triathlon), the platform enables a user to better choose a particular course and/or length (e.g., Ironman, Half Ironman, Olympic distance, and Sprint distance) to suit his or her strengths, or to challenge his or her weaknesses.

Thus, the platform enables an individual to predict his or her performance on an unfamiliar course based upon up-to-date course ratings and the individual's historic performance information on other courses. The information provided by the platform also allows the individual to more effectively train for an upcoming event on courses that are closer and more convenient to the individual. For example, course ratings allow a user to choose and train on courses that are similar in difficulty, leg-for-leg, to a course that will be used for an upcoming competition. The platform also enables a user to determine an individualized performance goal based on his or her historical performance information.

Moreover, the platform provides a updated ranking of athletes based on collective historical performance data gathered from users of the platform. The platform determines a rating—e.g., a par completion time or other performance standard—for each leg of a given course (e.g., analogous to "par" for a given hole at a given course). Ratings may be further determined as a function of a given class of athlete—e.g., a given age category, gender, and/or elite or non-elite status. Thus, an individual is able to challenge him or herself to beat the performance standard applicable to that individual based on one or more categories, for a given course at a given point in time (e.g., based on current course conditions).

In certain embodiments, the platform also allows for compensation of environmental conditions on the ratings for a given course. For example, upon entry by a user of performance data for a particular competition, course, and/or time, the platform may access weather information for that location and time and compensate for this information in the maintenance and/or determination of course and/or leg ratings.

Because course conditions may change over time, and because performance standards may change given improving performance of top athletes, the multi-user platform offers a way to account for those changes in real-time (or near real-time), for example, by providing updated course ratings. Furthermore, as an individual user enters more data as he or she performs more courses, the platform offers a way to track performance over time, such that improvement can be seen and quantified, even as the individual performs on different courses.

In one aspect, the present disclosure describes a method including receiving, over a network from a user of a remote computing device, a course performance submission. The course performance submission for one or all of the stages of a multiple stage sport activity, including completion time information, a user identifier, a course identifier, and contextual identifiers. The contextual identifiers include at least one of a stage identifier identifying the one or more stages of the multiple stage sport activity associated with the course performance submission, a competition identifier identifying a competition associated with the course performance submission, an ability level identifier identifying a user ability level associated with the course performance submission, and a distance rating identifier identifying a distance rating associated with the course performance submission. The method further includes accessing, by a processor of a computing device, one or more additional course performance submissions from multiple users, where the additional course performance submissions share the course identifier and at least one of the contextual identifiers. The method further includes determining, by the processor, based upon a portion of the course performance submissions received from the multiple users, an overall performance rating specific to each of the stages of the multiple stage sport activity. The method further includes providing, based upon at least one of the contextual identifiers and the overall performance rating, an individualized performance goal for at least one stage of the multiple stage sport activity.

In another embodiment, the multiple stage sport activity is a triathlon. In another embodiment, the one or more stages of the multiple stage sport activity comprise running, swimming, and bicycling. In another embodiment, the course identifier is determined based upon GPS location data. In another embodiment, the individualized performance goal is determined by adjusting the overall performance rating based upon the user ability level. In another embodiment, the overall performance rating is based on the subset of course performance submissions sharing a competition identifier. In another embodiment, the method further includes determining, based upon one or more course performance submissions sharing a user identifier and a distance rating, the user ability level associated with the user. In another embodiment, the user ability level comprises a stage ability level for each stage of the multiple stage sport activity. In another embodiment, the user ability level comprises a stage ability level for each of running, swimming, and bicycling.

In another aspect, the present disclosure describes a system including, a processor and a memory. The memory has instructions that cause the processor to receive, over a network from a user of a remote computing device, a course performance submission. The course performance submission for one or all of the stages of a multiple stage sport activity, including completion time information, a user identifier, a course identifier, and contextual identifiers. The contextual identifiers include at least one of a stage identifier identifying the one or more stages of the multiple stage sport activity associated with the course performance submission, a competition identifier identifying a competition associated with the course performance submission, an ability level identifier identifying a user ability level associated with the course performance submission, and a distance rating identifier identifying a distance rating associated with the course performance submission. The instructions further cause the processor to access one or more additional course performance submissions from multiple users, where the additional course performance submissions share the course identifier and at least one of the contextual identifiers. The instructions further cause the processor to determine, based upon a portion of the course performance submissions received from the multiple users, an overall performance rating specific to each of the stages of the multiple stage sport activity. The instructions further cause the processor to provide, based upon at least one of the contextual identifiers and the overall performance rating, an individualized performance goal for at least one stage of the multiple stage sport activity.

BRIEF DESCRIPTION OF THE FIGURES

The foregoing and other objects, aspects, features, and advantages of the present disclosure will become more apparent and better understood by referring to the following description taken in conjunction with the accompanying drawings, in which.

Figure 1:
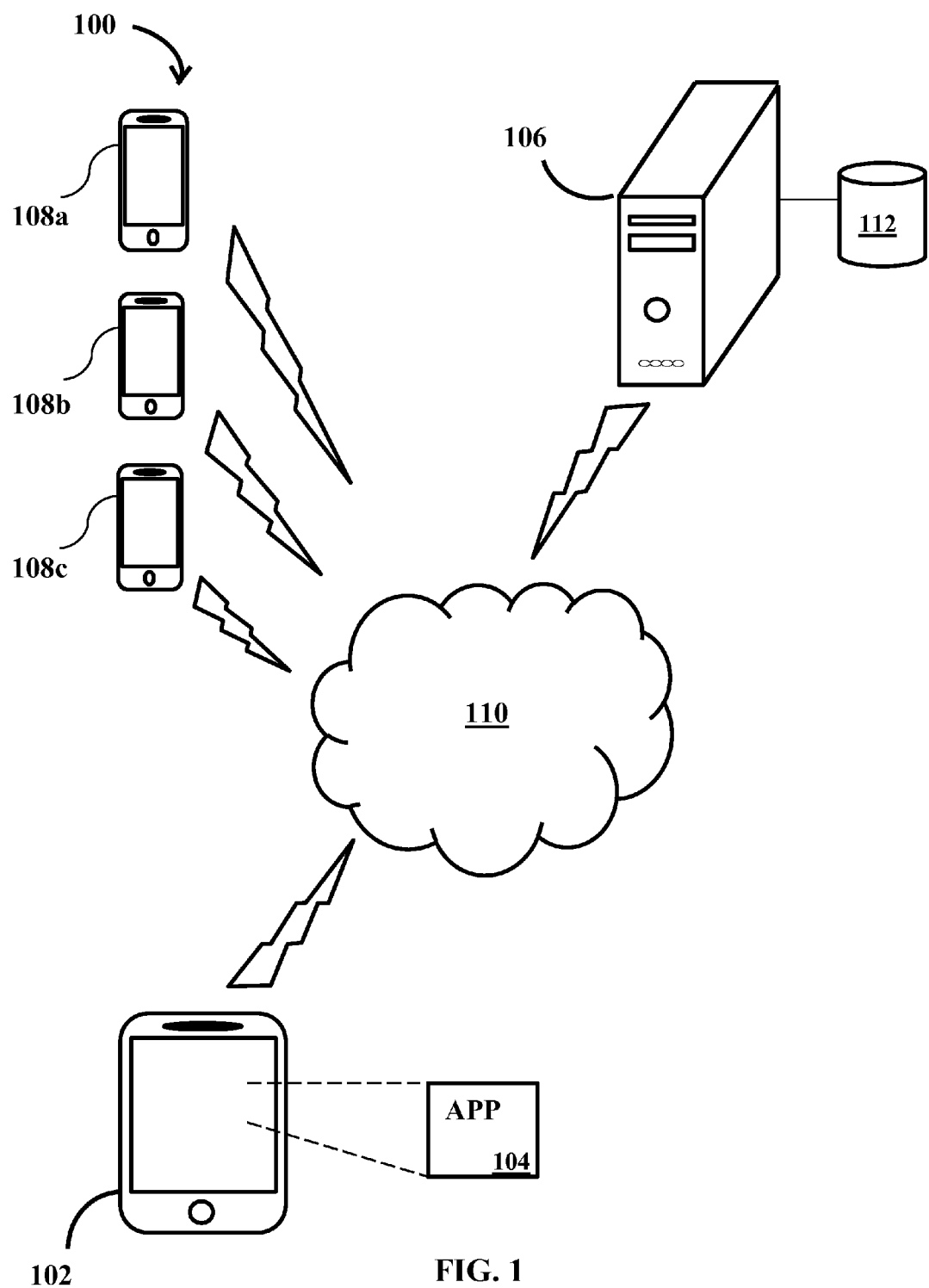
FIG. 1 is a diagram of a system for determining an individualized performance goal for a multiple stage sport activity, according to an illustrative embodiment of the invention.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

The present disclosure presents a system, method, and computer-program product directed toward the determination and maintenance of performance ratings for particular courses and/or stages of a multiple stage sport activity, as well as determination of individualized goals based on those ratings and individual historical performance data. In some implementations, multiple stage sport activities may include, but are not limited to, triathlons, duathlons, off-road triathlons and duathlons, aquathlons, biathles, aquabikes, quadrathlons, decathlons, rowathlons, and winter triathlons and quadrathlons. Examples of stages represented in multiple stage sport activities include swimming, bicycling, running, skiing, and shooting.

The system of the present disclosure allows users to contribute to an overall performance rating that reflects, based upon historical performance data for a plurality of users, a par completion time for individual stages of the multiple stage sport activity and for the total completion time of the multiple stage sport activity. Based upon a user's own historical performance data and other contextual factors, the platform calculates a 'handicap' and/or an individualized performance goal for the user, according to the user's ability level and/or other factors.

FIG. 1 is a diagram of a system for determining and/or maintaining an individualized performance goal for a multiple stage sport activity, according to an illustrative embodiment of the invention. The mobile environment 100 provides multiple users with the infrastructure to calculate an individualized performance goal. A mobile device 102 is in communication with the application server 106 via the network 110. The application server 110 includes a processor and a memory, and is configured to access a storage volume 112 to store course performance data submissions submitted by the user via his or her mobile device 102 and other users via their mobile devices 108a, 108b, and 108c (collectively, the other mobile devices 108). Mobile device 102 presents a mobile application 104, which is used, amongst other things, to create performance data submissions by the user.

The mobile device 102 may include a timer, which can be activated and deactivated by the user for each of the various stages of the multiple stage sport activity. For example, a user who is performing a triathlon will typically perform a swimming stage, a bicycling stage, and a running stage. The user interacts with the mobile application 104 to initiate the swimming stage timer (using, for example, a large button labeled "Start Triathlon Timer"). During the transition to the bicycling stage, the user interacts with the mobile application 104 to cease the swimming stage timer and initiate a bicycling stage timer (using, for example, the same large button, relabeled by the mobile application 104 to "Start Bicycle Stage"). During the transition to the running stage, the user interacts with the mobile application 104 to cease the swimming stage timer and initiate a running stage timer (using, for example, the same large button, relabeled by the mobile application 104 to "Start Running Stage"). After completion of the running stage, the user interacts with the mobile application 104 to end the running timer and complete the triathlon (using, for example, the same large button, relabeled by the mobile application 104 to "Stop Triathlon Timer"). The mobile application 104 thus has the necessary data to determine the completion time for each of the stages of the triathlon, and further has the necessary data to determine the overall completion time for the triathlon (i.e., by summing the completion times for each of the three stages.)

In some implementations, the user does not interact with the mobile application 104 during the multiple stage sport activity; he or she simply initiates the timer at the beginning of the activity, and ceases the timer after the completion of all stages of the activity in order to determine an overall completion time. In further implementations, the mobile device 102 is configured to transition the timer between stages of the multiple stage sport activity using alternative methods. Some examples of alternative methods for interacting with the timer include, but are not limited to, voice activated commands, use of physical buttons on the mobile device, GPS checkpoints or local wireless checkpoints at the course transition locations, and separate devices (such as the Garmin Forerunner racing computer or Samsung Galaxy Gear watch computer) configured to interact with the mobile device 102 and mobile application 104 using a wired connection (e.g., headphone jack connections or USB connections) or a wireless connection (e.g., Wi-fi or Bluetooth). In certain implementations, the mobile device 102 further includes sensors such as an accelerometer and/or a gyroscopic sensor, and the mobile application 104 is configured to interpret the readings of the sensors to detect when a particular activity is being performed.

In some implementations, certain stages of the multiple stage sport activity may be non-timed stages or stages including an additional scoring element not entirely dependent on completion time (e.g., a rifle marksmanship stage.) The user is further enabled to input the additional scoring information during or after the completion of the multiple stage sport activity.

After completion of a multiple stage sport activity, the course performance information is sent by the mobile application 104 to the application server 106. The application server 106 is configured to store the performance data on the storage volume 112 so that it can be used to suggest an individualized performance goal for future multiple stage sport activities and/or competitions. In some implementations, the performance data is also stored on the mobile device 102.

Figure 2:
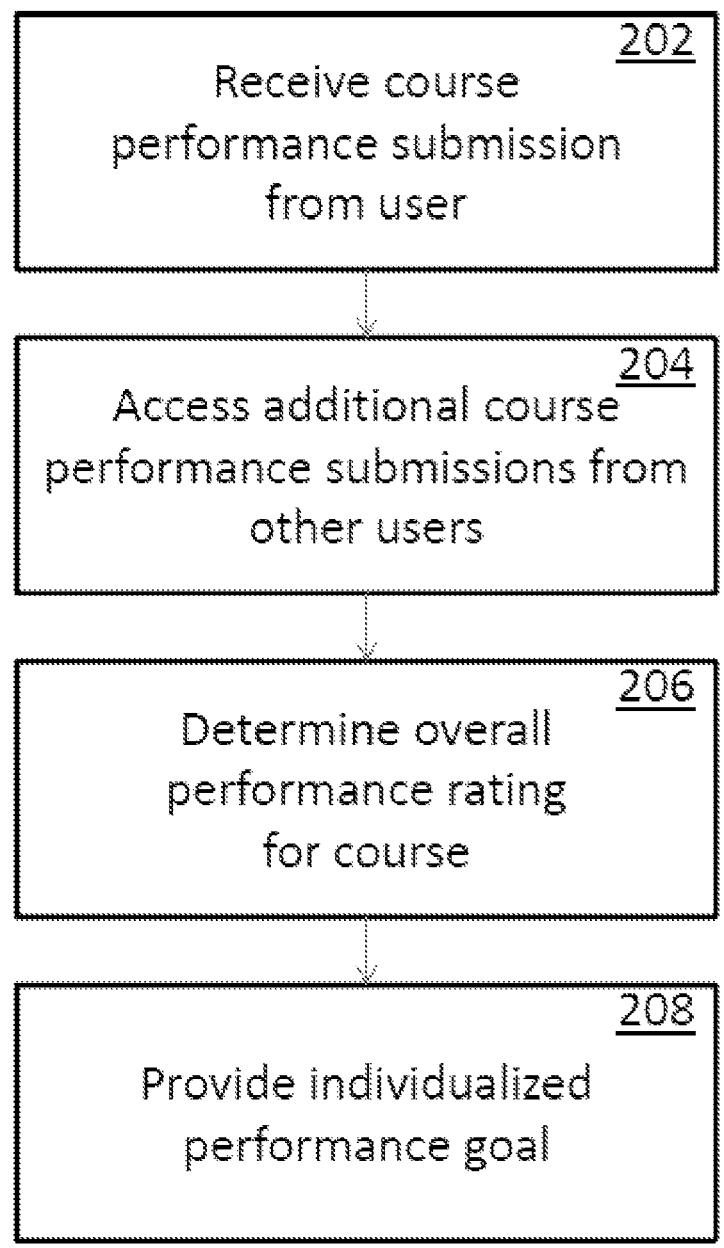
FIG. 2 is a block diagram illustrating a method of providing an individualized performance goal for a multiple stage sport activity, according to an illustrative embodiment of the invention.

FIG. 2 is a block diagram illustrating a method of providing an individualized performance goal for a multiple stage sport activity, according to an illustrative embodiment of the invention. The application server 106 receives, over a network, a course performance submission from the user of a mobile device 102 [202]. The course performance submission includes a variety of data that can be used to determine an overall performance rating and an individualized performance goal to the user. The course performance submission includes the completion time and any additional scoring associated with each of the one or more stages of the multiple stage sport activity that the user has completed.

In one implementation, the user completes an entire multiple stage sport activity (such as a triathlon), and the course performance submission includes completion time data for each of the stages (e.g., 120 minutes for the swimming stage, 480 minutes for the bicycling stage, and 360 minutes for the running stage) and the total completion time for the multiple stage sport activity (e.g., 960 minutes total time for the triathlon). In some implementations, the course performance submission may further include additional scoring data for certain stages of the multiple stage sport activity that are non-timed stages or stages that include an additional scoring element not entirely dependent on completion time (e.g., 18 hits out of 24 attempts for a rifle marksmanship stage.)

The user may also choose not to complete the entire multiple stage sport activity, and the course performance submission will include only the completion time or scoring for the particular stages that the user has completed. For example, a user training for an Ironman Triathlon competition may wish to specifically work on the bicycling stage in order to improve his or her performance on that particular stage. The user is enabled to submit only the completion time for the bicycling stage for use in the determination of an individualized performance goal for the bicycling stage.

Each course performance submission includes a user identifier linking the course performance submission to a unique user. The application server 106 stores the course performance submission on storage volume 112, enabling the application server 106 to access historical course performance data when determining the individualized performance goal for the unique user.

Each course performance submission includes a course identifier linking the course performance submission to a particular course (such as the Ironman Arizona triathlon course in Tempe, Arizona and the Ironman Mallorca triathlon course in Mallorca, Spain). The course identifier is used by the application server to determine an overall performance rating for the particular course, by analyzing a plurality of course performance submissions linked by the particular course identifier. The resultant overall performance rating is used by the application server to determine the individualized performance goal for a unique user on the particular course. In some implementations, the course identifier is tied to a location. In further implementations, the course identifier is determined using the GPS capabilities of the mobile device 102.

The course performance submission further includes at least one contextual identifier, which is used by the application server to determine an overall performance rating or individualized performance goal. Examples of contextual identifiers include, but are not limited to, a stage identifier identifying the one or more stages of the multiple stage sport activity associated with the course performance submission (e.g., the swimming stage, the bicycle stage, the running stage, or combinations thereof), a competition identifier identifying a competition associated with the course performance submission (e.g., the Ironman Mallorca competition in Mallorca, Spain or the Ironman 70.3 Boulder competition in Boulder, Colo.), an ability level identifier identifying a user ability level associated with the course performance submission (e.g., a high or low ability level relative to other users), and a distance rating identifier identifying a distance rating associated with the course performance submission (e.g., a full Ironman triathlon, a half Ironman triathlon, or an Ironkids triathlon).

In certain implementations, the ability level identifier is determined based on a user's relative performance level compared to other users. For example, the application server 106 may analyze all of the course performance submissions corresponding to the Ironman Mallorca triathlon course identifier to determine the average course completion time for each of the one or more stages of the course. Users who perform the triathlon in a time less than the average course completion time may be categorized as high performance ability level, and users who exceed the average course completion time may be categorized as low performance ability level. In some implementations, users are assigned an ability level by the application server at a higher granularity, up to and including individual ranking of performance level (e.g., the 54th highest ability level out of 2,500 unique users at the particular course). In further implementations, users are assigned an ability level independent of a particular course (e.g., an 80th percentile ability level worldwide). In other implementations, an overall ability level coefficient is determined for each stage of the multiple stage sport activity. For example, for a triathlon, a three value coefficient may be determined representing performance ability on each stage of the activity (e.g., a coefficient value of (0.8, 0.5, 0.7) corresponds to how well the user performs on swimming, bicycling, and running, respectively).

After receiving a course performance submission, the application server 106 accesses a plurality of additional performance submissions that share at least one contextual identifier [204]. For example, when a user submits a course performance submission corresponding to the bicycle stage of a triathlon, the application server is configured to analyze only those submissions from users who have also completed the bicycle stage of the triathlon. The applications server may consider those submissions where the bicycle stage was completed exclusively, or may further consider submissions where the bicycle stage was completed in combination with other stages.

In another example, when a user submits a course performance submission corresponding to a particular competition, the application server may analyze only those submissions by users who were also competing in the exact same competition, or those submissions by users who were competing in the same competition or a previous iteration of the competition. Such an analysis is useful for determining an overall performance rating for when the plurality of users are competing "at their best" as opposed to the more general data obtained when users are training for the competition.

In some implementations, users are enabled to configure which identifiers will be used for the analysis and determination of the overall performance rating and individualized performance goal. For example, users may wish to determine an overall performance goal based only upon other users at an ability level within a threshold distance from their own ability level. In another example, a user may wish to determine an individualized performance goal that is based only upon those submissions where the user completed the bicycle stage of a triathlon exclusively.

After accessing the plurality of course performance submissions corresponding to one or more contextual identifiers, the application server determines an overall performance rating for each particular stage of the multiple stage sport activity [206]. In some implementations, the application server further limits its analysis to a subset of course performance submissions, such as a competition identifier. In certain implementations, the application server analyzes all submissions corresponding to a particular course identifier and one or more contextual identifiers. In other implementations, the application server only considers a single submission per analysis for each unique user (such as the best submission), or the average all of the submissions received from a unique user.

The overall performance rating indicates a course performance that, in general, represents a successful course completion (similar to achieving a "par" score in Golf). In some implementations, the application server calculates an average course completion time based upon the course identifier and one or more contextual identifiers, and uses the average as the overall course rating. Thus, the course performance rating corresponds to the completion time of an average user. In other implementations, the course performance rating is calculated based upon only a subset of performance submissions. For example, the application server may analyze only those submissions by users in the 75th percentile of course completion times when determining the course performance rating. An overall performance rating is determined for each of the stages of the multiple stage sport activity and for the complete multiple stage sport activity. In some implementations, a course performance rating is represented by a coefficient that indicates how difficult a course is compared to other courses for each stage of the activity (e.g., for a triathlon, a course performance rating coefficient of (0.8, 1.3, 0.9) indicates the relative difficult of the course compared to other triathlon courses for each of swimming, biking, and running, respectively). In certain implementations, the course performance rating is based upon the rate of progress during the performance (e.g., a course performance rating corresponding to swimming at 100 m/s).

The application server is further enabled to provide, based upon at least one of the contextual identifiers, an individualized performance goal for one or more stages of the multiple stage sport activity [208]. Users vary in their relative ability level, and an overall performance rating which is ideal for a particular user may be too easy or too hard to achieve for another user. The individualized performance goal takes into account at least one historical data point for the unique user and the overall performance rating. Based on the user's ability level, the individualized performance goal presents a goal that should be achievable for the user but still instills satisfaction in the user when it is achieved. In a preferred embodiment, the application server deducts (or adds) a time modification value to the overall performance rating of the course. For example, a high ability level user on a 960 minute overall performance rating course may be given a 40 minute deduction, resulting in an individualized performance goal of 920 minutes. If the user achieves or exceeds the goal, he or she may consider himself or herself to have successfully completed the course (similar to applying a golf handicap to an overall score after a round of golf). In further implementations, the individualized performance goal serves as a predictor of expected performance based on the historical data associated with a unique user and his or her prior performance submissions. In certain implementations, the historical data and corresponding contextual identifiers enable the application server to offer a prediction of course performance on courses that the user has never previously completed.

In some implementations, the individualized performance goal and/or overall performance rating may further utilize the distance identifier to enabled users to compare multiple stage sport activities of the same type (e.g., triathlon) which, though of different distances, can still be useful to predict performance and establish goals. For example, a user who performs a half Ironman course may be able to get a useful prediction for his or her performance on a full Ironman course.

Figure 3:
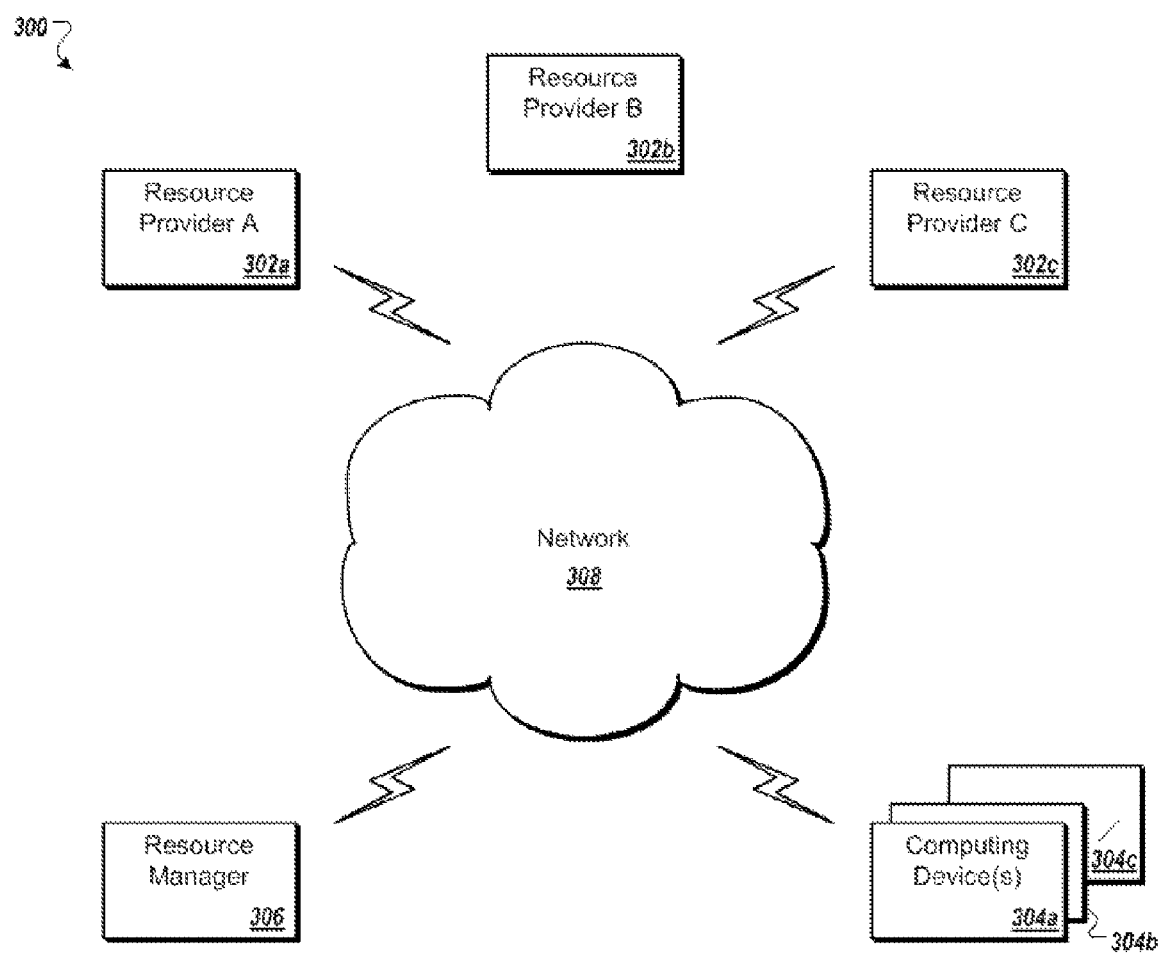
FIG. 3 is a block diagram of an example network environment, according to an illustrative embodiment.

FIG. 3 shows an illustrative network environment 300 for use in the methods and systems for analysis of spectrometry data corresponding to particles of a sample, as described herein. In brief overview, referring now to FIG. 3, a block diagram of an exemplary cloud computing environment 300 is shown and described. The cloud computing environment 300 may include one or more resource providers 302a, 302b, 302c (collectively, 302). Each resource provider 302 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 302 may be connected to any other resource provider 302 in the cloud computing environment 300. In some implementations, the resource providers 302 may be connected over a computer network 308. Each resource provider 302 may be connected to one or more computing device 304a, 304b, 304c (collectively, 304), over the computer network 308.

The cloud computing environment 300 may include a resource manager 306. The resource manager 306 may be connected to the resource providers 302 and the computing devices 304 over the computer network 308. In some implementations, the resource manager 306 may facilitate the provision of computing resources by one or more resource providers 302 to one or more computing devices 304. The resource manager 306 may receive a request for a computing resource from a particular computing device 304. The resource manager 306 may identify one or more resource providers 302 capable of providing the computing resource requested by the computing device 304. The resource manager 306 may select a resource provider 302 to provide the computing resource. The resource manager 306 may facilitate a connection between the resource provider 302 and a particular computing device 304. In some implementations, the resource manager 306 may establish a connection between a particular resource provider 302 and a particular computing device 304. In some implementations, the resource manager 306 may redirect a particular computing device 304 to a particular resource provider 302 with the requested computing resource.

Figure 4:
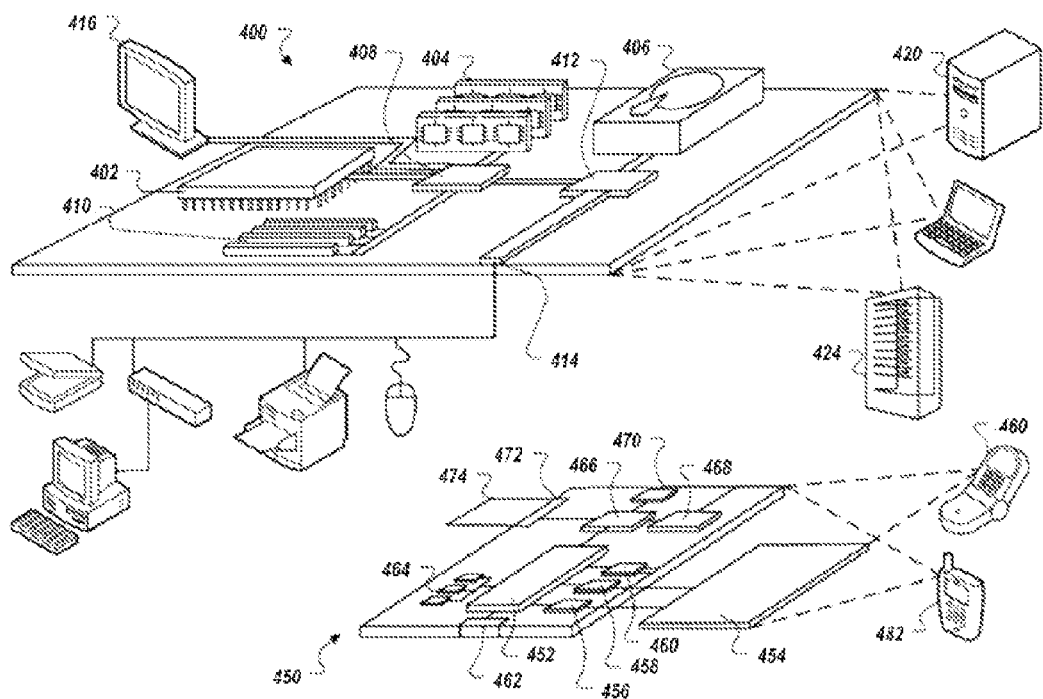
FIG. 4 is a block diagram of an example computing device and an example mobile computing device, for use in illustrative embodiments of the invention.

FIG. 4 shows an example of a computing device 400 and a mobile computing device 450 that can be used in the methods and systems described in this disclosure. The computing device 400 is intended to represent various forms of digital computers, such as laptops, desktops, workstations, personal digital assistants, servers, blade servers, mainframes, and other appropriate computers. The mobile computing device 450 is intended to represent various forms of mobile devices, such as personal digital assistants, cellular telephones, smartphones, and other similar computing devices. The components shown here, their connections and relationships, and their functions, are meant to be examples only, and are not meant to be limiting.

The computing device 400 includes a processor 402, a memory 404, a storage device 406, a high-speed interface 408 connecting to the memory 404 and multiple high-speed expansion ports 410, and a low-speed interface 412 connecting to a low-speed expansion port 414 and the storage device 406. Each of the processor 402, the memory 404, the storage device 406, the high-speed interface 408, the high-speed expansion ports 410, and the low-speed interface 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as a display 416 coupled to the high-speed interface 408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 404 stores information within the computing device 400. In some implementations, the memory 404 is a volatile memory unit or units. In some implementations, the memory 404 is a non-volatile memory unit or units. The memory 404 may also be another form of computer-readable medium, such as a magnetic or optical disk.

The storage device 406 is capable of providing mass storage for the computing device 400. In some implementations, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 402), perform one or more methods, such as those described above. The instructions can also be stored by one or more storage devices such as computer- or machine-readable mediums (for example, the memory 404, the storage device 406, or memory on the processor 402).

The high-speed interface 408 manages bandwidth-intensive operations for the computing device 400, while the low-speed interface 412 manages lower bandwidth-intensive operations. Such allocation of functions is an example only. In some implementations, the high-speed interface 408 is coupled to the memory 404, the display 416 (e.g., through a graphics processor or accelerator), and to the high-speed expansion ports 410, which may accept various expansion cards (not shown). In the implementation, the low-speed interface 412 is coupled to the storage device 406 and the low-speed expansion port 414. The low-speed expansion port 414, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. In addition, it may be implemented in a personal computer such as a laptop computer 422. It may also be implemented as part of a rack server system 424. Alternatively, components from the computing device 400 may be combined with other components in a mobile device (not shown), such as a mobile computing device 450. Each of such devices may contain one or more of the computing device 400 and the mobile computing device 450, and an entire system may be made up of multiple computing devices communicating with each other.

The mobile computing device 450 includes a processor 452, a memory 464, an input/output device such as a display 454, a communication interface 466, and a transceiver 468, among other components. The mobile computing device 450 may also be provided with a storage device, such as a microdrive or other device, to provide additional storage. Each of the processor 452, the memory 464, the display 454, the communication interface 466, and the transceiver 468, are interconnected using various buses, and several of the components may be mounted on a common motherboard or in other manners as appropriate.

The processor 452 can execute instructions within the mobile computing device 450, including instructions stored in the memory 464. The processor 452 may be implemented as a chipset of chips that include separate and multiple analog and digital processors. The processor 452 may provide, for example, for coordination of the other components of the mobile computing device 450, such as control of user interfaces, applications run by the mobile computing device 450, and wireless communication by the mobile computing device 450.

The processor 452 may communicate with a user through a control interface 458 and a display interface 456 coupled to the display 454. The display 454 may be, for example, a TFT (Thin-Film-Transistor Liquid Crystal Display) display or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may provide communication with the processor 452, so as to enable near area communication of the mobile computing device 450 with other devices. The external interface 462 may provide, for example, for wired communication in some implementations, or for wireless communication in other implementations, and multiple interfaces may also be used.

The memory 464 stores information within the mobile computing device 450. The memory 464 can be implemented as one or more of a computer-readable medium or media, a volatile memory unit or units, or a non-volatile memory unit or units. An expansion memory 474 may also be provided and connected to the mobile computing device 450 through an expansion interface 472, which may include, for example, a SIMM (Single In Line Memory Module) card interface. The expansion memory 474 may provide extra storage space for the mobile computing device 450, or may also store applications or other information for the mobile computing device 450. Specifically, the expansion memory 474 may include instructions to carry out or supplement the processes described above, and may include secure information also. Thus, for example, the expansion memory 474 may be provided as a security module for the mobile computing device 450, and may be programmed with instructions that permit secure use of the mobile computing device 450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 452), perform one or more methods, such as those described above. The instructions can also be stored by one or more storage devices, such as one or more computer- or machine-readable mediums (for example, the memory 464, the expansion memory 474, or memory on the processor 452). In some implementations, the instructions can be received in a propagated signal, for example, over the transceiver 468 or the external interface 462.

The mobile computing device 450 may communicate wirelessly through the communication interface 466, which may include digital signal processing circuitry where necessary. The communication interface 466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 468 using a radio-frequency. In addition, short-range communication may occur, such as using a Bluetooth®, Wi-Fi™, or other such transceiver (not shown). In addition, a GPS (Global Positioning System) receiver module 470 may provide additional navigation- and location-related wireless data to the mobile computing device 450, which may be used as appropriate by applications running on the mobile computing device 450.

The mobile computing device 450 may also communicate audibly using an audio codec 460, which may receive spoken information from a user and convert it to usable digital information. The audio codec 460 may likewise generate audible sound for a user, such as through a speaker, e.g., in a handset of the mobile computing device 450. Such sound may include sound from voice telephone calls, may include recorded sound (e.g., voice messages, music files, etc.) and may also include sound generated by applications operating on the mobile computing device 450.

The mobile computing device 450 may be implemented in a number of different forms, as shown in the figure. For example, it may be implemented as a cellular telephone 480. It may also be implemented as part of a smart-phone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method comprising:
receiving, over a network from a user of a first computing device, a first course performance submission comprising a) completion time information for one or more stages of a multiple stage sport activity having two or more stages, b) a user identifier identifying a first competitor, c) a course identifier, and d) one or more contextual identifiers, wherein each stage of the two or more stages of the multiple stage sport activity comprises one of a plurality of different sporting category event types, and wherein the one or more contextual identifiers comprise one or more of:
   (i) a stage identifier identifying the one or more stages of the multiple stage sport activity associated with the first course performance submission,
   (ii) a competition identifier identifying a competition associated with the first course performance submission,
   (iii) an ability level identifier identifying a user ability level of the first competitor associated with the first course performance submission, and
   (iv) a distance rating identifier identifying a distance rating associated with the first course performance submission;
accessing, by a processor of a second computing device, one or more second course performance submissions from a plurality of second competitors, wherein the one or more second course performance submissions share the course identifier associated with the first course performance submission and at least one of the contextual identifiers associated with the first course performance submission;
determining, by the processor of the second computing device, based upon the first course performance submission and a subset of the one or more second course performance submissions received from the plurality of second competitors, an overall performance rating specific to each of the two or more stages of the multiple stage sport activity; and
providing, by the processor of the second computing device, based upon at least one of the contextual identifiers and the overall performance rating, an individualized performance goal for at least one stage of the two or more stages of the multiple stage sport activity for the first competitor by adjusting the overall performance rating based on the user ability level of the first competitor.

2. The method of claim 1, wherein the multiple stage sport activity is a triathlon.

3. The method of claim 1, wherein the multiple stage sport activity is a member selected from the group consisting of biathlon, decathlon, heptathlon, modern pentathlon, octathlon, pentathlon, quadrathlon, and tetrathlon.

4. The method of claim 1, wherein the two or more stages of the multiple stage sport activity comprise running, swimming, and bicycling.

5. The method of claim 1, wherein the course identifier is determined based upon one or more members of the group consisting of: GPS location data, wireless broadcasting data, and digital location data through mobile data.

6. The method of claim 1, wherein the overall performance rating is based on the subset of second course performance submissions sharing a competition identifier.

7. The method of claim 1, further comprising determining, by the processor of the second computing device, based upon one or more course performance submissions sharing a user identifier and a distance rating, the user ability level associated with the first competitor.

8. The method of claim 1, wherein the user ability level comprises a stage ability level for each stage of the multiple stage sport activity.

9. The method of claim 1, wherein the user ability level comprises a stage ability level for each of running, swimming, and bicycling.

10. The method of claim 1, wherein the user ability level comprises a stage ability level for a plurality of the two or more stages of the multiple stage sport activity.

11. A system comprising:
a processor of a first computing device; and
a memory device having instructions stored thereon, wherein the instructions, when executed by the processor, cause the processor to:
receive, over a network from a user of a second computing device, a first course performance submission comprising a) completion time information for one or more stages of a multiple stage sport activity having two or more stages, b) a user identifier identifying a first competitor, c) a course identifier, and d) one or more contextual identifiers, wherein each stage of the two or more stages of the multiple stage sport activity comprises one of a plurality of different sporting category event types, and wherein the one or more contextual identifiers comprise at least one of:
   i) a stage identifier identifying the one or more stages of the multiple stage sport activity associated with the first course performance submission,
   ii) a competition identifier identifying a competition associated with the first course performance submission,
   iii) an ability level identifier identifying a user ability level of the first competitor associated with the first course performance submission, and
   iv) a distance rating identifier identifying a distance rating associated with the first course performance submission;
access one or more second course performance submissions from a plurality of second competitors, wherein the one or more second course performance submissions share the course identifier associated with the first course performance submission and at least one of the contextual identifiers associated with the first course performance submission;
determine, based upon the first course performance submission and a subset of the one or more second course performance submissions received from the plurality of second competitors, an overall performance rating specific to each of the two or more stages of the multiple stage sport activity; and
provide, based upon at least one of the contextual identifiers and the overall performance rating, an individualized performance goal for at least one stage of the two or more stages of the multiple stage sport activity for the first competitor by adjusting the overall performance rating based on the user ability level of the first competitor.

12. The system of claim 11, wherein the multiple stage sport activity is a triathlon.

13. The system of claim 11, wherein the multiple stage sport activity is a member selected from the group consisting of biathlon, decathlon, heptathlon, modern pentathlon, octathlon, pentathlon, quadrathlon, and tetrathlon.

14. The system of claim 11, wherein the two or more stages of the multiple stage sport activity comprise running, swimming, and bicycling.

15. The system of claim 11, wherein the course identifier is determined, by the processor, based upon one or more members of the group consisting of: GPS location data, wireless broadcasting data, and digital location data through mobile data.

16. The system of claim 11, wherein the overall performance rating is based on the subset of second course performance submissions sharing a competition identifier.

17. The system of claim 11, wherein the instructions cause the processor to determine, based upon one or more course performance submissions sharing a user identifier and a distance rating, the user ability level associated with the first competitor.

18. The system of claim 11, wherein the user ability level comprises a stage ability level for each stage of the multiple stage sport activity.

19. The system of claim 11, wherein the user ability level comprises a stage ability level for each of running, swimming, and bicycling.

20. The system of claim 11, wherein the user ability level comprises a stage ability level for a plurality of the two or more stages of the multiple stage sport activity.

\* \* \* \* \*